United States Patent
McBrady et al.

(10) Patent No.: US 9,128,028 B2
(45) Date of Patent: Sep. 8, 2015

(54) THERMAL CONDUCTIVITY DETECTORS

(75) Inventors: Adam D. McBrady, Minneapolis, MN (US); Robert Higashi, Shorewood, MN (US); Karen M. Newstrom-Peitso, Hopkins, MN (US); Fouad Nusseibeh, Champlin, MN (US)

(73) Assignee: Honeywell International Inc., Morristown, NJ (US)

( * ) Notice: Subject to any disclaimer, the term of this patent is extended or adjusted under 35 U.S.C. 154(b) by 362 days.

(21) Appl. No.: 12/846,506

(22) Filed: Jul. 29, 2010

(65) Prior Publication Data

US 2012/0024043 A1    Feb. 2, 2012

(51) Int. Cl.
*G01N 25/18* (2006.01)
*G01N 27/18* (2006.01)
*G01N 30/66* (2006.01)

(52) U.S. Cl.
CPC ............... *G01N 27/18* (2013.01); *G01N 30/66* (2013.01)

(58) Field of Classification Search
CPC ............................. G01N 27/18; G01N 30/66
USPC ............................................ 73/25.03; 374/44
See application file for complete search history.

(56) References Cited

U.S. PATENT DOCUMENTS

| | | | |
|---|---|---|---|
| 4,164,862 A | 8/1979 | Jackson | |
| 4,185,490 A | 1/1980 | Clouser et al. | |
| 4,215,564 A | 8/1980 | Lawson et al. | |
| 4,464,925 A | 8/1984 | Kolloff | |
| 5,165,292 A * | 11/1992 | Prohaska | 73/866 |
| 5,295,389 A | 3/1994 | Nagata et al. | |
| 5,379,630 A | 1/1995 | Lacey | |
| 5,482,372 A * | 1/1996 | Bataillard et al. | 374/31 |
| 5,581,028 A * | 12/1996 | Barth et al. | 73/204.26 |
| 5,587,520 A | 12/1996 | Rhodes | |
| 5,756,878 A * | 5/1998 | Muto et al. | 73/25.03 |
| 5,772,321 A * | 6/1998 | Rhodes | 374/44 |
| 6,010,243 A | 1/2000 | Hessler et al. | |
| 6,502,983 B2 | 1/2003 | Yu | |
| 6,550,325 B1 * | 4/2003 | Inushima et al. | 73/204.26 |
| 6,550,961 B1 | 4/2003 | Ueda | |
| 6,896,406 B2 | 5/2005 | Gellert | |
| 6,928,858 B2 | 8/2005 | Lin | |
| 6,981,410 B2 * | 1/2006 | Seki et al. | 73/204.26 |
| 7,096,729 B2 * | 8/2006 | Repko et al. | 73/204.26 |
| 7,117,736 B2 * | 10/2006 | Kamiunten et al. | 73/204.15 |
| 7,185,527 B2 | 3/2007 | Lin | |
| 7,347,080 B2 * | 3/2008 | Mahoney et al. | 73/23.4 |
| 7,350,971 B2 * | 4/2008 | Egolf et al. | 374/44 |
| 7,452,126 B2 * | 11/2008 | Arndt et al. | 374/44 |
| 7,485,176 B2 * | 2/2009 | Bentley et al. | 96/105 |
| 2001/0012313 A1 | 8/2001 | Yu | |

(Continued)

OTHER PUBLICATIONS

J. R. Olson et al., "Thermal conductivity of diamond between 170 and 1200K and the isotope effect", Physical Review, B, v. 47, pp. 14850-14856.*

*Primary Examiner* — Peter Macchiarolo
*Assistant Examiner* — Natalie Huls
(74) *Attorney, Agent, or Firm* — Brooks, Cameron & Huebsch, PLLC (57) ABSTRACT

Thermal conductivity detectors and methods of operating thermal conductivity detectors are described herein. One or more device embodiments include a single fluidic channel, wherein the single fluidic channel includes a single inlet and a single outlet, and multiple sensors configured to determine one or more properties associated with a thermal conductivity of a fluid in the single fluidic channel.

18 Claims, 2 Drawing Sheets

(56) References Cited

U.S. PATENT DOCUMENTS

| | | |
|---|---|---|
| 2004/0136435 A1 | 7/2004 | Gellert |
| 2004/0245993 A1 | 12/2004 | Bonne |
| 2004/0250601 A1 | 12/2004 | Lin |
| 2006/0236751 A1 | 10/2006 | Lin |
| 2006/0289809 A1* | 12/2006 | Bonne et al. .............. 250/504 R |
| 2007/0144238 A1 | 6/2007 | Mahoney et al. |
| 2008/0069178 A1 | 3/2008 | Bentley et al. |
| 2008/0291996 A1 | 11/2008 | Pateux et al. |
| 2009/0193872 A1* | 8/2009 | Tokuda et al. ............... 73/23.31 |
| 2011/0146398 A1* | 6/2011 | Beck et al. ................. 73/204.27 |

* cited by examiner

Fig. 2

# THERMAL CONDUCTIVITY DETECTORS

GOVERNMENT RIGHTS

The subject matter of this disclosure was made with government support under Subcontract No.: 61-000740 awarded by the SRI Stanford Research Institute. Accordingly, the U.S. Government has certain rights to subject matter disclosed herein.

TECHNICAL FIELD

The present disclosure relates to thermal conductivity detectors and methods of operating thermal conductivity detectors.

BACKGROUND

Chromatography, e.g., gas chromatography, gas-liquid chromatography, and/or liquid chromatography, can include separating and/or analyzing the components of a mixture. For example, chromatography can include separating one or more analytes in a mixture, and determining the concentration of the analyte(s), e.g., the relative amount of the analyte(s), in the mixture. An analyte can be, for example, an element and/or compound separated from a mixture for measurement and/or analysis, such as a gas, a liquid, or a combination thereof.

A thermal conductivity detector is one type of device than can be used in chromatography to analyze the components of a mixture. Thermal conductivity detectors can produce a signal that is proportional to the concentration and thermal conductivity of the analyte. For example, thermal conductivity detectors can give equal responses from a high concentration analyte with a low thermal conductivity and a low concentration analyte with a high thermal conductivity. With calibration, thermal conductivity detectors can be used in gas chromatography and/or gas-liquid chromatography to determine the concentration of one or more analytes separated from a mixture.

A thermal conductivity detector can provide high sensitivity for large analyte concentrations. That is, thermal conductivity detectors can distinguish small differences in concentration among highly concentrated analytes. Additionally, a thermal conductivity detector can be a universal detection mechanism. For example, thermal conductivity detectors can determine the concentration of any type of analyte, so long as the analyte's thermal conductivity is different from that of the chromatographic carrier fluid (typically He, $N_2$, or $H_2$).

Previous thermal conductivity detectors can determine the concentration of an analyte by performing a differential measurement using a reference fluid, e.g., a reference gas and/or liquid that contains just a chromatographic carrier fluid and not any analyte. That is, previous thermal conductivity detectors can be referenced and/or differential thermal conductivity detectors. For example, a previous thermal conductivity detector can determine, e.g., measure, the difference in thermal conductivity between a reference fluid and a fluid under analysis that may contain an analyte. The concentration of the analyte can then be determined using the measured thermal conductivity difference. This difference can be more accurate in that it can account for drifts in sensor response caused by internal and/or external effects, e.g., power supply and/or temperature changes.

However, the reference fluid used to perform the differential measurement in the previous thermal conductivity detector can change the composition of the fluid under analysis, which can pose difficulties for any subsequent detectors. For example, a previous thermal conductivity detector may dilute the analyte, e.g., with the reference fluid, by combining both fluids during the course of measurement. Hence, subsequent measurements and/or analysis performed on the fluid by additional detectors may be less reliable and/or accurate, due to the change in composition, e.g., dilution of the fluid under analysis.

Accordingly, additional detectors may be unsuitable to measure and/or analyze the analyte after a previous thermal conductivity detector performs a differential measurement using a reference fluid. This may occur as a result of the subsequent detector being influenced significantly by the flow perturbations caused by the reference fluid existing in the previous thermal conductivity detector. In one case, these perturbations could manifest themselves as a signal oscillation in a subsequent detector that is proportional to the subsequent detector's signal. These and similar incompatibilities can prevent additional detectors from being successfully used in series with previous thermal conductivity detectors that perform a differential measurement using a reference fluid, because the reference fluid may change the fluid's composition and/or flow characteristics.

Additionally, other embodiments of previous thermal conductivity detectors that perform differential measurements using a reference fluid can avoid changing the composition and/or flow characteristics of the fluid under analysis by adding complexity, and/or increasing the number of components of the detector itself, because additional components may be needed to accommodate the reference fluid. The additional hardware required in such a differential measurement can be undesirable from a cost and/or portability standpoint.

Further, previous thermal conductivity detectors that perform a differential measurement using a reference gas may have a low data collection rate, e.g., less than 50 Hertz, because such previous thermal conductivity detectors may have a relatively large size and/or large thermal mass. Such low data collection rates may not be suitable for some high speed and/or high throughput applications.

DETAILED DESCRIPTION

Thermal conductivity detectors and methods of operating thermal conductivity detectors are described herein. One or more device embodiments include a single fluidic channel, wherein the single fluidic channel includes a single inlet and a single outlet, and multiple sensors configured to determine one or more properties associated with a thermal conductivity of a fluid in the single fluidic channel.

Thermal conductivity detectors in accordance with one or more embodiments of the present disclosure may not change the composition of, e.g., dilute, an analyte during the process of measuring the fluid. The composition of the fluid under analysis is maintained throughout the measurement process because thermal conductivity detectors in accordance with the present disclosure may be non-referenced and/or non-differential. Accordingly, additional detectors may be used in series with the non-referenced and/or non-differential thermal conductivity detectors described herein.

Thermal conductivity detectors in accordance with one or more embodiments of the present disclosure may have a reduced size, complexity, and/or number of components as compared to previous thermal conductivity detectors. Thermal conductivity detectors in accordance with the present disclosure may be fabricated to have low thermal mass sensing elements and correspondingly high data collection rates, e.g., at rates of 50 Hertz or greater.

In the following detailed description, reference is made to the accompanying drawings that form a part hereof. The drawings show by way of illustration how one or more embodiments of the disclosure may be practiced. These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present invention, and should not be taken in a limiting sense.

As used herein, "a" or "a number of" something can refer to one or more such things. For example, "a number of sensors" can refer to one or more sensors.

Figure 1A:
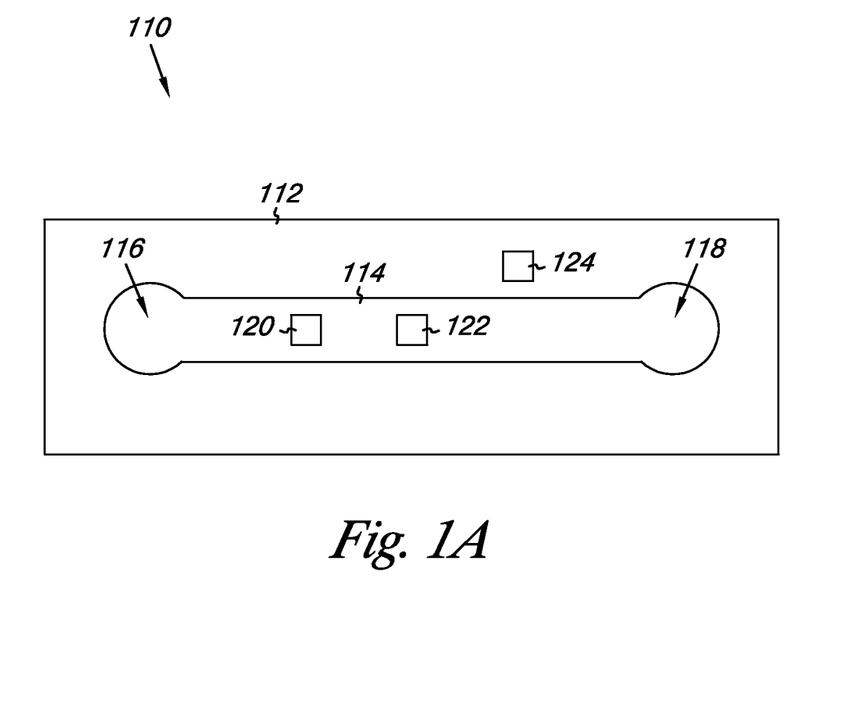
FIG. 1A illustrates a schematic top view of a thermal conductivity detector, with a top-cap wafer of the thermal conductivity detector not shown for clarity, in accordance with one or more embodiments of the present disclosure.
Figure 1B:
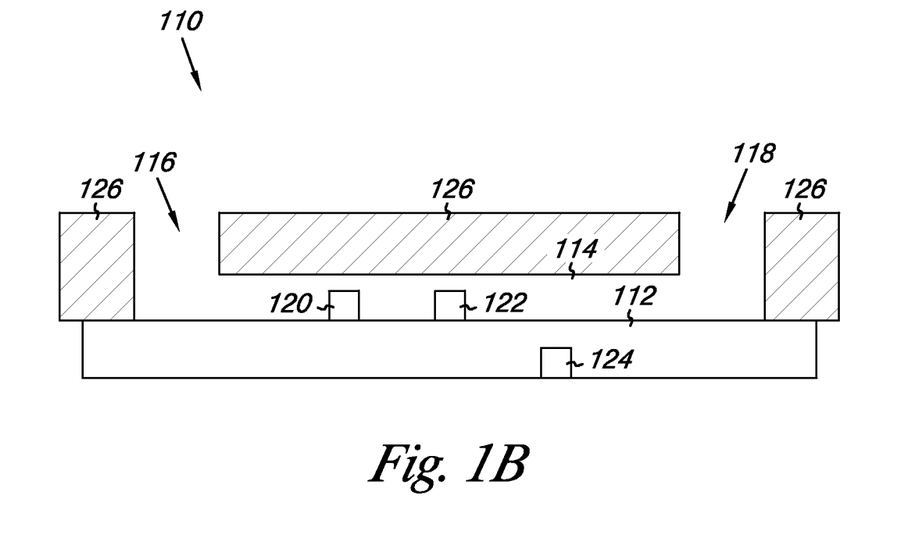
FIG. 1B illustrates a schematic cross-sectional view of a thermal conductivity detector in accordance with one or more embodiments of the present disclosure.

FIG. 1A illustrates a schematic top view of a thermal conductivity detector 110, with a top-cap wafer 126 of thermal conductivity detector 110 not shown for clarity, in accordance with one or more embodiments of the present disclosure. FIG. 1B illustrates a schematic cross-sectional view of thermal conductivity detector 110 in accordance with one or more embodiments of the present disclosure.

As shown in FIGS. 1A and 1B, thermal conductivity detector 110 includes a single fluidic channel 114 having a single inlet 116 and a single outlet 118. A fluid, as used herein, can be, for example, a gas, a liquid, and/or a combination thereof. Fluidic channel 114 can be formed by bonding a top-cap wafer 126 to a bottom wafer 112. Bottom wafer 112 can be functionalized to contain a number of sensors 120, 122, and 124. Wafers 112 and 126 can be, for example, silicon wafers, among other suitable wafer materials. Embodiments of the present disclosure are not limited to a particular type of wafer. FIGS. 1A and 1B illustrate a single thermal conductivity detector assembled from two wafers, e.g., wafers 112 and 126. In practice, multiple thermal conductivity detectors can be fabricated simultaneously via standard photolithographic techniques. After fabrication and wafer bonding, the boded wafers can be diced, separating the multiple detectors. In this manner, one wafer may contain multiple thermal conductivity devices, e.g., a second portion of wafer 112 and a second fluidic channel can be associated with a second thermal conductivity detector, a third portion of wafer 112 and a third fluidic channel can be associated with a third thermal conductivity detector, etc. In one or more embodiments, twenty thermal conductivity detectors can be fabricated on wafer 112. Embodiments of the present disclosure are not limited to a particular number of thermal conductivity detectors. After bulk fabrication and dicing, the thermal conductivity detectors can be wire bonded onto electronic interface boards before use.

As shown in FIG. 1B, fluidic channel 114 can be formed by bonding top-cap wafer 126 to bottom wafer 112. Fluidic channel 114 includes a single inlet 116 and a single outlet 118. Inlet 116 and outlet 118 can be, for example, holes that are etched through top-cap wafer 126 prior to bonding wafers 112 and 126.

The fluid to be analyzed by thermal conductivity detector 110 can be introduced into fluidic channel 114 via inlet 116. The fluid can flow through fluidic channel 114, interact with sensors 120, 122, and/or 124, and exit fluidic channel 114 via outlet 118. The fluid to be analyzed can be, for example, the effluent from a gas chromatograph that contains a number of analytes separated in time with a background carrier fluid, as will be further described in connection with FIG. 2.

As shown in FIGS. 1A and 1B and discussed above, thermal conductivity detector 110 includes sensors 120, 122, and 124. Each sensor 120, 122, and 124 can determine, e.g., sense, a property associated with the thermal conductivity of a fluid in fluidic channel 114. For example, a sensor can determine a rate of flow, temperature, and/or pressure, among other properties, associated with the fluid in fluidic channel 114 or the material of wafer 112. For instance, sensor 124 can be a temperature sensor for wafer 112, and the temperature of wafer 112 can be used in conjunction with the properties sensed by sensors 120 and/or 122 to determine the thermal conductivity of the fluid in fluidic channel 114. Although three sensors are illustrated in FIGS. 1A and 1B, embodiments of the present disclosure can include any number of sensors. In one or more embodiments of the present disclosure, the raw signals from the flow and temperature sensors can be used in conjunction with the power supplied to the flow and temperature sensors. In this manner, the flow and temperature sensors can be used as constant temperature heaters and/or constant power heaters. This ability can allow sensors 120, 122, and/or 124 to sense properties associated the thermal conductivity of the fluid in fluidic channel 114. Additionally, multiple sensors may be used to sense the same property or properties, or the sensors may sense different properties.

In the embodiment illustrated in FIGS. 1A and 1B, sensors 120 and 122 can be situated to measure properties of the fluid within fluidic channel 114. Sensor 124 is outside of fluidic channel 114 and can measure a property, e.g., background temperature, of detector 110. The raw signals from and energy used by sensors 120, 122, and/or 124 can be used to adjust the responses from sensors 120 and 122 in order to compensate for environmentally induced signal deviations. The combination of the signals from sensors 120, 122, and/or 124 can be combined to give a single value that is proportional to the thermal conductivity of the fluid in fluidic channel 114.

Properties, e.g., rate of flow, temperature, pressure, and/or energy used to maintain a temperature of the fluid in fluidic channel 114 sensed by sensors 120, 122, and/or 124 can be used to identify the average thermal conductivity of the fluid under analysis. The individual sensor responses can be sent, via digital signals, from sensors 120, 122, and/or 124 to additional circuitry and/or one or more computing devices (not shown in FIG. 1A or 1B). The additional circuitry and/or computing devices can compare the collective responses of sensors 120, 122, and 124 to a previously recorded calibration and identify the fluid and/or determine a concentration associated with an analyte within the fluid.

In one or more embodiments, sensors 120 and 122 can be flow sensors that can determine a rate of flow of a fluid through fluidic channel 114, temperature sensors that can determine a temperature of a fluid in fluidic channel 114, and/or pressure sensors that can determine a pressure of a fluid in fluidic channel 114. Sensor 124 can be a heat-sunk temperature sensor that can determine the temperature of wafer 112, and therefore the surrounding environment.

Embodiments of the present disclosure, however, are not limited to a particular type and/or combination of sensors. For example, sensors 120, 122, and/or 124 can be any type of sensor that can sense any type of property associated with the thermal conductivity of a fluid in fluidic channel 114.

Sensors 120, 122, and/or 124 can be located within fluidic channel 114, within the portion of wafer 112, e.g., outside fluidic channel 114, and/or a combination thereof. For example, in the embodiment illustrated in FIGS. 1A and 1B, sensors 120 and 122 are located within fluidic channel 114, and sensor 124 is located within the portion of wafer 112, but outside fluidic channel 114.

Embodiments of the present disclosure, however, are not limited to a particular location for sensors 120, 122, and 124. For example, any and/or all of sensors 120, 122, and 124 can be located within fluidic channel 114 or outside fluidic channel 114 but within the portion of wafer 112 associated with a particular thermal conductivity detector.

In one or more embodiments, thermal conductivity detector 110 can be a non-referenced thermal conductivity detector. That is, sensors 120, 122, and/or 124 of thermal conductivity detector 110 can sense one or more properties associated with the thermal conductivity of a fluid in thermal conductivity detector 110, e.g., fluidic channel 114, without using a reference fluid. For example, thermal conductivity detector 110 may not use an additional reference fluid to determine the thermal conductivity of the fluid under analysis. Accordingly, the identity and/or concentration of the fluid in thermal conductivity detector 110 can be determined without using a reference fluid.

In one or more embodiments, thermal conductivity detector 110 can be a non-differential thermal conductivity detector. That is, thermal conductivity detector 110 can determine one or more properties associated with the thermal conductivity of a fluid in thermal conductivity detector 110 without performing a differential measurement, e.g., without performing a measurement in which a difference between two quantities is determined. For example, each sensor 120, 122, and 124 can determine the one or more properties associated with the thermal conductivity of the fluid in thermal conductivity detector 110 by sensing single quantities and combining those quantities to create a single value that is proportional to the thermal conductivity of the fluid under analysis. Accordingly, the composition of the fluid in thermal conductivity detector 110 may remain unchanged while in thermal conductivity detector 110, as will be further described herein.

Thermal conductivity detector 110 can be a non-referenced and/or non-differential thermal conductivity detector, and/or thermal conductivity detector 110 may not change the composition of, e.g., dilute, a fluid while the fluid is in thermal conductivity detector 110. For example, thermal conductivity detector 110 can determine one or more properties associated with the thermal conductivity of a fluid in fluidic channel 114 without performing a differential measurement using a reference fluid. Therefore, thermal conductivity detector 110 can determine the thermal conductivity of a fluid under analysis without diluting the fluid, e.g., with a reference fluid. Further, thermal conductivity detector 110 can determine the thermal conductivity of the fluid without creating flow perturbations in the fluid that could disrupt the performance of a subsequent detector.

Because the fluid in thermal conductivity detector 110 may not be changed, e.g., diluted, while in thermal conductivity detector 110, the reliability and/or accuracy of subsequent measurements and/or analysis performed on the fluid by additional detectors after the fluid exits thermal conductivity detector 110 may not be affected. Accordingly, additional detectors may be used to measure and/or analyze the fluid after the fluid exits thermal conductivity detector 110. That is, additional detectors may be used in series with thermal conductivity detector 110, as will be further described in connection with FIG. 2. In contrast, additional detectors may be not be used in series with previous thermal conductivity detectors, as previously described herein.

Additionally, because thermal conductivity detector 110 can be a non-referenced and/or non-differential thermal conductivity detector, thermal conductivity detector 110 may have a reduced size, complexity, and/or number of components as compared to previous thermal conductivity detectors. For example, because thermal conductivity detector 110 can determine one or more properties associated with the thermal conductivity of a fluid in thermal conductivity detector 110 without performing a differential measurement using a reference fluid, thermal conductivity detector 110 may not include additional fluidic channels, inlets, and/or outlets, and/or other components that would be needed to accommodate a reference fluid. That is, thermal conductivity detector 110 can include a single fluidic channel, a single inlet, and a single outlet, as illustrated in FIGS. 1A and 1B.

For example, thermal conductivity detector 110 can be a microelectromechanical system (MEMS) based device. The size of sensors 120, 122, and/or 124 within thermal conductivity detector 110 can be on the order of a micrometer. The small size of sensors 120, 122, and/or 124 within fluidic channel 114 can present a small thermal mass. The low thermal mass of sensors 120, 122, and/or 124 within thermal conductivity detector 110 can allow the fluid under analysis to rapidly affect sensors 120, 122, and/or 124. This, in turn, can allow for fast data acquisition rates of greater than 50 Hertz.

In contrast, previous thermal conductivity detectors, e.g., referenced and/or differential thermal conductivity detectors, may have an increased size, complexity, and/or number of components as compared to thermal conductivity detector 110. For example, because previous thermal conductivity detectors may perform a differential measurement using a reference fluid, previous thermal conductivity detectors may include multiple fluidic channels, inlets, and/or outlets, and/or other components to accommodate the reference fluid. Further, the size of previous thermal conductivity detectors may be greater than the order of a micrometer, and/or previous thermal conductivity detectors may have a high thermal mass and correspondingly slow data acquisition rates.

Additionally, in some embodiments, sensors 120, 122, and/or 124 of thermal conductivity detector 110 can determine one or more properties associated with the thermal conductivity of a fluid in thermal conductivity detector 110, e.g., in fluidic channel 114, at a frequency of approximately 50 Hertz, due to, for example, the small size and/or low thermal mass of sensors 120, 122, and/or 124 That is, thermal conductivity detector 110 can have a data collection rate of greater than 50 Hertz. Further, sensors 120, 122, and/or 124 can respond to a change, e.g., a step change, in the properties in less than 20 milliseconds. In contrast, previous thermal conductivity detectors may have data collection rates of less than 50 Hertz, which may not be suitable for some applications, e.g., fast chromatograms whose peaks are less than 20 milliseconds in width.

Those of ordinary skill in the art will understand that thermal conductivity detectors can include additional components not illustrated in FIGS. 1A and 1B, but such components are not illustrated so as not to obscure the illustrated components of the present disclosure. For example, thermal conductivity detector 110 can include electrical connections coupled to wafer 112, fluidic channel 114, and/or sensors 120, 122, and/or 124, as will be appreciated by one of ordinary skill in the art. The electrical connections can, for example, transport signals, e.g., electrical and/or digital signals, to and/or from thermal conductivity detector 110.

Figure 2:
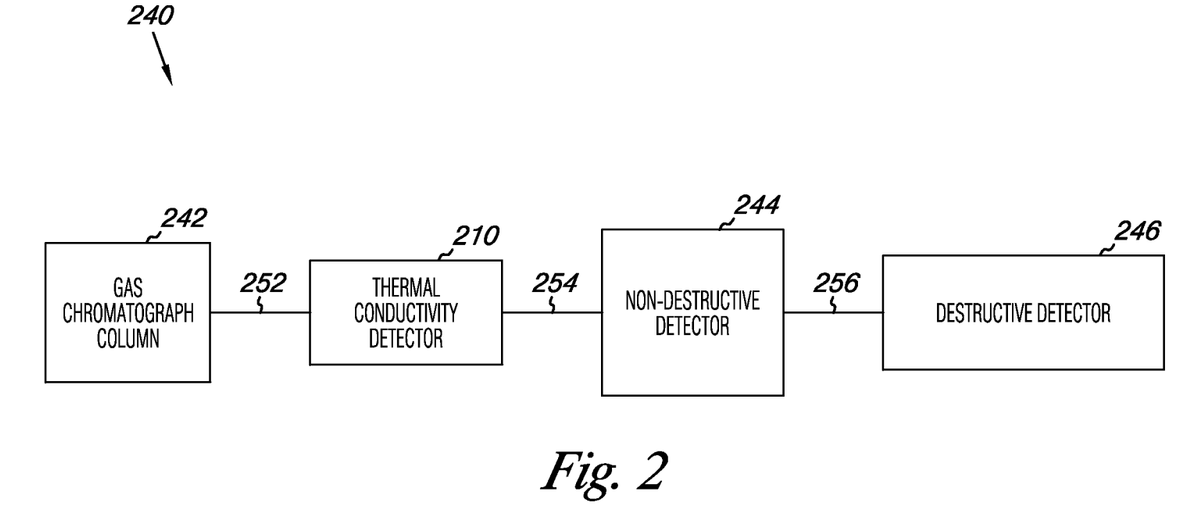
FIG. 2 illustrates a block diagram of a detection system in accordance with one or more embodiments of the present disclosure.

FIG. 2 illustrates a block diagram of a detection system 240 in accordance with one or more embodiments of the present disclosure. As shown in the embodiment illustrated in FIG. 2, detection system 240 includes a gas chromatograph column 242, a thermal conductivity detector 210, a non-destructive detector 244, and a destructive detector 246 coupled in series. For example, thermal conductivity detector 210 can be coupled in series to gas chromatograph column 242 by a first fluid, e.g., gas, connection line 252, non-destructive detector 244 can be coupled in series to thermal conductivity detector 210 by a second fluid connection line 254, and destructive detector 246 can be coupled in series to non-destructive detector 244 by a third fluid connection line 256, as illustrated in FIG. 2.

In one or more embodiments, thermal conductivity detector 210 can be, for example, thermal conductivity detector 110 described in connection with FIG. 1. That is, thermal conductivity detector 210 can be a non-referenced and/or non-differential thermal conductivity detector in accordance with one or more embodiments of the present disclosure.

Non-destructive detector 244 can be a detector that does not destroy and/or consume a component it detects. For example, non-destructive detector 244 can be a resonator-array based detector relying on unique polymer phases to distinguish analyte classes, among other types of non-destructive detectors. In one or more embodiments, non-destructive detector 244 can be an additional thermal conductivity detector.

Embodiments of the present disclosure are not limited to a particular number and/or type of non-destructive detectors. That is, detection system 240 can include any number of non-destructive detectors. For example, non-destructive detector 244 can be coupled in series to a second non-destructive detector, a third non-destructive detector can be coupled in series to the second destructive detector, etc., and the final non-destructive detector in the series can be coupled to destructive detector 246.

Destructive detector 246 can be a detector that destroys and/or consumes a component it detects. For example, destructive detector can be a mass spectrometer, among other types of destructive detectors. Because destructive detector 246 may destroy and/or consume a component it detects, destructive detector 246 may be the last detector in the series, as illustrated in FIG. 2.

In various embodiments, such as the embodiment illustrated in FIG. 2, gas chromatograph column 242 can be utilized to separate an analyte from a mixture, as will be appreciated by one of skill in the art. The analyte can be, for example, a fluid, such as a gas, a liquid, and/or a combination thereof.

The separated analyte can be sent from gas chromatograph 242 to thermal conductivity detector 210 via fluid connection line 252. Upon receiving the analyte, thermal conductivity detector 210 can determine one or more properties associated with the thermal conductivities of the separated analytes and/or the concentrations of the analytes in the separated mixture without changing the composition of, e.g., diluting, the chromatographic effluent and/or the analytes therein, as described in connection with FIG. 1.

Because the analyte may not be diluted by thermal conductivity detector 210, the analyte can be sent to additional detectors for additional measurement and/or analysis after thermal conductivity detector 210 determines one or more properties associated with the analyte, as described in connection with FIG. 1. For example, the analyte can be sent from thermal conductivity detector 210 to a non-destructive detector, e.g., non-destructive detector 244, for additional measurement and/or analysis. The analyte can also be sent from non-destructive detector 244 to destructive detector 246, or sent from a thermal conductivity detector, e.g., thermal conductivity detector 210, to a destructive detector, for additional measurement and/or analysis.

Those of ordinary skill in the art will understand that detection systems can include additional components not illustrated in FIG. 2, but such components are not illustrated so as not to obscure the illustrated components of the present disclosure. For example, detection system can include one or more data collectors coupled to thermal conductivity detector 210, non-destructive detector 244, and/or destructive detector 246. The one or more data collectors can be, for example, one or more computing devices provided and configured to collect data from thermal conductivity detector 210, non-destructive detector 244, and/or destructive detector 246, as will be appreciated by one of skill in the art. The collected data can be, for example, the one or more properties associated with the analyte and/or the concentration of the analyte in the mixture determined by thermal conductivity detector 210, among other data.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A detection system, comprising:
a thermal conductivity detector, wherein the thermal conductivity detector includes:
    a single fluidic channel formed by a first wafer and a second wafer such that the single fluidic channel includes a single inlet and a single outlet having a width greater than a width of the single fluidic channel between the single inlet and the single outlet; and
    multiple sensors configured to determine one or more properties associated with a thermal conductivity of a fluid in the single fluidic channel and determine an identity and concentration of the fluid, wherein the multiple sensors include multiple flow sensors located within the single fluidic channel adjacent a single side of the single fluidic channel and configured to determine a rate of flow of the fluid through the single fluidic channel; and
a non-destructive detector coupled in series to the thermal conductivity detector, wherein the thermal conductivity detector is a non-differential thermal conductivity detector, and wherein the non-destructive detector receives the fluid from the thermal conductivity detector and performs additional analysis of the one or more properties, including a pressure, associated with the fluid.

2. The detection system of claim 1, wherein the multiple sensors include:
a temperature sensor configured to determine a temperature of the fluid in the single fluidic channel; and
a heat-sunk temperature sensor configured to determine a temperature of the first wafer or the second wafer.

3. The detection system of claim 1, wherein the multiple sensors include multiple temperature sensors located within the single fluidic channel and configured to determine a temperature of the fluid in the single fluidic channel.

4. The detection system of claim 1, wherein the multiple sensors include multiple heat-sunk temperature sensors configured to determine a temperature of the first wafer or the second wafer.

5. The detection system of claim 1, wherein the multiple sensors include a pressure sensor configured to determine the pressure of the fluid in the single fluidic channel.

6. The detection system of claim 1, wherein:
at least one of the multiple sensors is located within the first wafer or the second wafer, but outside the single fluidic channel.

7. The detection system of claim 1, wherein the multiple sensors are configured to respond to changes in the one or more properties in less than 20 milliseconds.

8. The detection system of claim 1, wherein the multiple sensors are configured to determine the one or more properties associated with the thermal conductivity of the fluid in the single fluidic channel using raw signals from the multiple sensors and power supplied to the multiple sensors.

9. A detection system, comprising:
a non-referenced thermal conductivity detector configured to determine one or more properties associated with a thermal conductivity of a fluid without diluting the fluid, wherein the non-referenced thermal conductivity detector includes:
    a single fluidic channel formed by a first wafer and a second wafer such that the single fluidic channel includes a single inlet and a single outlet having a width greater than a width of the single fluidic channel between the single inlet and the single outlet; and
    multiple sensors located within the single fluidic flow channel adjacent a single side of the single fluidic flow channel and determine an identity and concentration of the fluid, and wherein the multiple sensors are configured to determine a rate of flow of the fluid through the single fluidic channel;
a non-destructive detector coupled in series to the non-referenced thermal conductivity detector, wherein the thermal conductivity detector is a non-differential thermal conductivity detector, and wherein the non-destructive detector receives the fluid from the thermal conductivity detector and performs additional analysis of the one or more properties, including a pressure, associated with the fluid; and
a destructive detector coupled in series to the non-destructive detector.

10. The detection system of claim 9, wherein each of the multiple flow sensors have a size of 1 micrometer.

11. The detection system of claim 9, wherein the non-referenced thermal conductivity detector is a microelectromechanical system (MEMS) based device.

12. The detection system of claim 9, wherein the non-referenced thermal conductivity detector has a data acquisition rate of greater than 50 Hertz.

13. The detection system of claim 9, wherein the non-referenced thermal conductivity detector is configured to determine the properties associated with the thermal conductivity of the fluid without creating flow perturbations in the fluid.

14. The detection system of claim 9, wherein the properties associated with the thermal conductivity of the fluid include:
a rate of flow of the fluid through the non-referenced thermal conductivity detector;
a temperature of the fluid in the non-referenced thermal conductivity detector; and
the pressure of the fluid in the non-referenced thermal conductivity detector.

15. A method of operating a thermal conductivity detector, comprising:
determining a number of properties associated with a fluid in a single fluidic channel of the thermal conductivity detector using multiple sensors in the thermal conductivity detector, wherein:
    the single fluidic channel is formed by a first wafer and a second wafer such that the single fluidic channel includes a single inlet and a single outlet having a width greater than a width of the single fluidic channel between the single inlet and the single outlet;
    the number of properties include at least one of:
        a rate of flow of the fluid;
        a temperature of the fluid; and
        a pressure of the fluid; and
    the multiple sensors include multiple flow sensors located within the single fluidic channel adjacent a single side of the single fluidic channel and determine an identity and concentration of the fluid, and wherein the multiple sensors are configured to determine a rate of flow of the fluid through the single fluidic channel; and
sending the fluid from the thermal conductivity detector to a non-destructive detector coupled in series to the thermal conductivity detector after determining the properties, wherein the thermal conductivity detector is a non-differential thermal conductivity detector, and wherein the non-destructive detector receives the fluid from the thermal conductivity detector and performs additional analysis of the one or more properties, including the pressure, associated with the fluid.

16. The method of claim 15, wherein the method includes determining the properties without using a reference fluid.

17. The method of claim 15, wherein the method includes determining the properties by:
    sensing single quantities; and
    combining the single quantities to create a single value.

18. The method of claim 15, wherein the method includes determining the properties without changing the composition of the fluid.

* * * * *

UNITED STATES PATENT AND TRADEMARK OFFICE
CERTIFICATE OF CORRECTION

PATENT NO. : 9,128,028 B2
APPLICATION NO. : 12/846506
DATED : September 8, 2015
INVENTOR(S) : Adam D. McBrady et al.

It is certified that error appears in the above-identified patent and that said Letters Patent is hereby corrected as shown below:

In the specification Col. 1 line 5 should read:

"This invention was made with Government support under contract HR0011-09-C-0049 awarded by the Defense Advanced Research Projects Agency. The Government has certain rights in this invention."

Signed and Sealed this
First Day of March, 2016

Michelle K. Lee
*Director of the United States Patent and Trademark Office*